United States Patent [19]

Conti

[11] Patent Number: 4,985,410
[45] Date of Patent: Jan. 15, 1991

[54] QUATERNARY AMMONIUM SALTS OF POLYSACCHARIDES, PROSSESSING HYPOCHOLESTEROLEMIC ACTIVITY

[75] Inventor: Franco Conti, Milan, Italy

[73] Assignee: Etablissement Texcontor, Vaduz, Liechtenstein

[21] Appl. No.: 189,247

[22] Filed: May 2, 1988

Related U.S. Application Data

[63] Continuation of Ser. No. 801,323, Nov. 25, 1985, abandoned.

[30] Foreign Application Priority Data

Aug. 14, 1985 [IT] Italy .................. 21937 A/85

[51] Int. Cl.$^5$ .................. A61K 31/715; A61K 31/72; A61K 31/73
[52] U.S. Cl. .................. 514/54; 514/55; 514/57; 514/60; 536/20; 536/45; 536/52; 536/54; 536/50; 536/55.1; 536/114
[58] Field of Search .................. 514/54, 55, 57, 60; 536/20, 45, 43, 52, 55.3, 114, 50, 55.1, 54

[56] References Cited

U.S. PATENT DOCUMENTS

| | | | |
|---|---|---|---|
| 3,087,852 | 4/1963 | Hofreiter et al. | 536/45 |
| 3,380,998 | 4/1968 | Naito et al. | 536/31 |
| 3,472,840 | 10/1969 | Stone et al. | 536/43 |
| 3,505,310 | 4/1970 | Nordgren et al. | 536/52 |
| 3,769,399 | 10/1973 | Hagerman et al. | 424/79 |
| 3,892,731 | 7/1975 | Austin | 536/20 |
| 4,175,124 | 11/1979 | Hyldon et al. | 514/54 |
| 4,285,973 | 8/1981 | Edwards | 514/785 |
| 4,411,891 | 10/1983 | Mizutani et al. | 536/51 |
| 4,436,731 | 3/1984 | Maltz | 536/20 |
| 4,459,289 | 7/1984 | Maltz | 514/57 |
| 4,632,645 | 12/1986 | Matsunaga et al. | 536/45 |
| 4,708,951 | 11/1987 | Inagaki et al. | 514/57 |
| 4,726,809 | 2/1988 | DeBoer et al. | 536/45 |
| 4,758,282 | 7/1988 | Stober et al. | 536/114 |
| 4,792,415 | 12/1988 | Colegrove | 536/114 |

FOREIGN PATENT DOCUMENTS

| | | |
|---|---|---|
| 0066135 | 12/1982 | European Pat. Off. . |
| 0115574 | 8/1984 | European Pat. Off. . |
| 3301667 | 7/1984 | Fed. Rep. of Germany . |
| 53-126063 | 11/1978 | Japan . |
| 55-009673 | 1/1980 | Japan . |
| 55-73773 | 6/1980 | Japan . |
| 55-84504 | 6/1980 | Japan . |
| 55-127308 | 10/1980 | Japan . |
| 57-180602 | 11/1982 | Japan . |
| 1136842 | 12/1968 | United Kingdom . |
| 2094323 | 9/1982 | United Kingdom . |

OTHER PUBLICATIONS

Federal Register, 42, 37973 (Jul. 26, 1977). Chem. Abs., vol. 87, 116513v (1977).
Parkinson, J. Lipid Research 8, 24–29 (1967).
Yanagawa et al.; Chemical Abstracts 92:99446; (1980).
Abstracts Bulletin of the Institute of Paper Chemistry, vol. 51, no. 5, Nov. 1980, p. 524, Abstract No. 4779.
Chemical Abstracts, vol. 91, No. 22, Nov. 1979, p. 90, Abstract No. 176985t.
Chemical Abstracts, vol. 96, 1982, p. 55, Abstract No. 115788n.
Chemical Abstracts, vol. 89, No. 7, Aug. 14, 1978, p. 485, Abstract No. 58752a.
Hashim et al; JAMA 192(4):289-293 Apr. 26, 1965.
Kennedy; Adv. in Carb. Chem. Biochem. 29:315-329 (1974).

Primary Examiner—Johnnie R. Brown
Assistant Examiner—Nancy S. Carson
Attorney, Agent, or Firm—Stevens, Davis, Miller & Mosher

[57] ABSTRACT

Quaternary ammonium salts of polysaccharides possessing hypochlolesterolemic activity and having the following general formula:

$$\begin{array}{c} \vdash A \dashv_m \\ | \\ B-CH_2-CH-(CH_2)_n-N^{(+)}\!\!\!<\!\!\!\begin{array}{c}R\\R\\R\end{array} \quad X^{(-)} \\ | \\ OH \end{array} \quad (I)$$

in which A represents the monomer unit of a natural polysaccharide, m is a whole number between 100 and 1000, n is a whole number between 0 and 4, B is O or S or NH or NR, R is a linear alkyl radical of 1-4 carbon atoms, and $X^{(-)}$ is an anion such as $Cl^-$, $Br^-$, $I^-$, $HSO_4^-$, $CH_3O-SO_3^-$.

Said salts are prepared by reacting a pretreated natural polysaccharide with a a quaternary ammonium salt functionalized at one of its ends with an epoxy group.

13 Claims, No Drawings

QUATERNARY AMMONIUM SALTS OF POLYSACCHARIDES, PROSSESSING HYPOCHOLESTEROLEMIC ACTIVITY

This is a continuation of application Ser. No. 801,323, filed Nov. 25, 1985 now abandoned.

This invention relates to quaternary ammonium salts of polysaccharides, possessing hypocholesterolemic activity.

More particularly, the invention relates to water-soluble quaternary ammonium salts of polysaccharides of vegetable and microbic origin, of advantageous use in human therapy as hypocholesterolemic agents, to the process for their production, and to the relative pharmaceutical compositions.

The quaternary ammonium salts of polysaccharides according to the present invention have the following general formula:

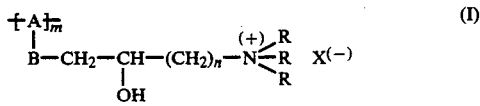

in which A represents the monomer unit of a natural polysaccharide, m is a whole number between 100 and 1000, n is a whole number between 0, and 4, B is 0 o S or NH or NR, R is a linear alkyl radical of 1-4 carbon atoms, and $X^{(-)}$ is an anion such as $Cl^-$, $Br^-$, $I^-$, $HSO_4^-$ of $CH_3O-SO_3^-$.

Generally, known products possessing hypocholesterolemic activity are cross-linked synthetic polymer derivatives, for example of polystyrene. These polymers are insoluble in water and thus their availability is extremely low, and in addition they have undesirable side effects.

Of the natural polymers, only suitably treated chitosan is used as a hypocholesterolemically active product.

However, in the known art (M. Sugano, T. Fujikawa et al., Am. J. of Clinical Nutrition, 33, April 1980, pp. 787, 793), the positive charges on the polysaccharide marcromolecules of the chitosan are obtained by simply protonizing the amino group, so that under the pH conditions of the intestinal tract (pH approximately 7.2), the proton is almost completely removed as the pKa of the chitosan is 6.3. For this reason the capacity of the polymer to interact with bile salts is very low.

In one of our previous patents (U.S. Pat. No. 4,436,731) the chitosan quaternisation reaction is conducted directly on the amino group present in the amino-glycoside ring, and the positive charge remains present under all pH and ionic force conditions of the gastrointestinal tract, however its closeness to the amino-glycoside ring creates accessibility problems for the bile salt molecules.

We have now discovered new water-soluble quaternary ammonium salts of polysaccharides, of which the positive charge is at a suitable distance from the polysaccharide macromolecule, on a branch which is easily available for interaction with the bile salt molecules.

Said salts, besides exercising a very intense hypocholesterolemic activity, are substantially free from toxicity on oral administration.

The quaternary ammonium salts of polysaccharides possessing hypocholesterolemic activity according to the present invention are characterized by being of formula (I) with a degree of substitution of between 0.5 and 2, and their preparation process is characterized by reacting a pretreated natural polysaccharide with a quaternary ammonium salt functionalized at one of its ends with an epoxy group able to react with nucleophilic groups of OH or SH or $NH_2$ or NHR type present in the polysaccharide macromolecule, and where R is a linear alkyl molecule containing 1-4 carbon atoms, in a reaction medium consisting of a mixed solvent.

These and further characteristics, both relative to the process for preparing the quaternary salts according to the invention and relative to their therapeutic applications, will be more apparent from the description given hereinafter of preferred embodiments of the invention, by way of non-limiting example.

The polysaccharides preferably used are tragacanth, guar and carob gums, and starch, cellulose, tamarind and chitosan.

Said polysaccharides are among the most representative of those available, and can be either water-insoluble such as cellulose or chitosan, or water-soluble such as guar gum, carob gum and starch.

The water-insoluble polysaccharides are previously hydrolysed by acid hydrolysis in order to obtain polymers with a suitable molecular weight, of between 50,000 and 300,000, or are dissolved in suitable solvents (for example the cellulose in dissolved in cupriethylenediamine and the chitosan is dissolved in formic acid) and then precipitated in an aqueous environment at pH 10-12 to obtain an almost amorphous polymer which is also able to react in the heterogeneous phase.

The water-soluble polysaccharides are previously activated by treatment with sodium hydroxide solutions of 10-30% concentration by weight, and are then dispersed in an organic solvent of for example the dioxane, acetone, ethyl alcohol or isopropyl alcohol type, to obtain NaOH-polysaccharide complexes which are very reactive towards the epoxy compounds.

The reaction between the polysaccharide and the epoxy compound is conducted in a mixed solvent, consisting for example of 15% water and 75% isopropyl alcohol under agitation, at a temperature of between 40° C. and 100° C., for a time of between 4 and 16 hours, with a molar ratio of polysaccharide to epoxy compound of between 1:1 and 1:6 and a weight ratio of polysaccharide to reaction medium of between 1:5 and 1:35.

The degree of substitution is between 0.5 and 2. The following examples and tables, relate respectively to the process for preparing compounds of general formula (I) and to their therapeutic applications, are given hereinafter for non-limiting illustration purposes.

EXAMPLE 1

100 g of commercial chitosan with a 20% degree of acetylation are dissolved in 5 liters of 0.1 M formic acid and the solution heated under reflux for 24 hours.

The solution is then cooled and precipitated by treating with 10 liters of 5N NaOH, the precipitate is filtered off, washed with isopropyl alcohol until its water content is 30%, and is then dispersed in 600 ml of isopropyl alcohol.

The system is kept under agitation for 40 minutes and 262 g of glycidyltrimethyl ammonium chloride are added, and the mixture heated to 80° C. for 6 hours.

The mixture is cooled and petroleum ether is added, the precipitate is filtered off and washed repeatedly with acetone and then dried under vacuum, to obtain 255 g of dry product.

The degree of substitution, determined by $^1$H-NMR, is 1.5

The water solubility of the product is 12% by weight at 25° C.

EXAMPLE 2

100 g of powdered guar gum are dispersed in 2 liters of a 20 weight % NaOH solution, and the system kept under agitation at ambient temperature for 1 hour.

The system is then dispersed in 3 liters of dioxane, 95 g of glycidyltrimethyl ammonium chloride are added, and the mixture kept under agitation at 40° C. for 24 hours.

The product is then precipitated by treatment with acetone, is washed repeatedly with acetone and petroleum ether, and finally dried under vacuum to obtain 250 g of dry product.

The degree of substitution, determined by $^1$H-NMR, is equal to 1.4 and its water solubility is 15% by weight at 25° C.

EXAMPLE 3

100 g of cellulose powder previously hydrolyzed with 0.1 M HCl and swollen in 2000 ml of 0.5 M cupriethylenediamine at ambient temperature are regenerated in 100 ml of acetone.

The cellulose is repeatedly washed in mixtures of water and acetone and is then immersed in an 8 weight % solution of NaOH and then squeeze-dried and dispersed in 2 liters of 95% ethanol.

150 g of propyleneoxide triethylammoniumbromide are added and the mixture heated to 80° C. for 24 hours.

After cooling, the product is precipitated by treatment with petroleum ether, is filtered off, washed with acetone and then dried under vacuum.

The degree of substitution, determined by $^1$H-NMR, is 0.9, and the water solubility at 25° C. is 7% by weight.

Using the aforesaid methods, quaternary ammonium salts were prepared from powdered carob gum, starch, tamarind and tragacanth.

The products according to the present invention were used in a series of pharmacological tests, the results of which are summarized in the following tables. For comparison purposes the results are also given of tests carried out under the same conditions with cholestyramine, which is the most effective resin of hypocholesterolemic activity currently available.

The following test was used to demonstrate the "in vivo" hypocholesterolemic effect of the various resins: Action on the hypercholesterolemia induced in the rat and rabbit by a cholesterol-enriched diet.

To induce hypercholesterolemia in rats, the animals were kept under a Nath diet (Nath and coll., J. Nutrit. 67, 289, 1959) containing:

devitaminized casein: 20%
DL-methionine: 0.4%
Hegsted saline mixture: 4%
Saccharose: 49.1%
Cholesterol: 1%
Cholic acid: 0.5% and vitamins Hypercholesterolemia was induced in the rabbits by administering 1g/animal/day of cholesterol with a gastric probe Sprague-Dawley rats with an average weight of 200 g and New Zealand rabbits weighing 3 kg were used, divided into groups of 10 animals each.

All the animals were made hypercholesterolemic by means of the diet. One group remained untreated and served as the controls, whereas the other groups were treated with 0.5 g/kg of the various products under examination for 30 days.

After 30 days of treatment all the animals were killed and the total plasmatic cholesterol in the blood collected from the carotid arteries was determined (Pearson and coll. J. Chim. Endocrin. Metabolism 12, 1245, 1952).

Tables 1 and 2 summarized the results obtained on the rats and rabbits made hypercholesterolemic by diet, and treated with the various indicated products.

The products according to the invention which were used in these tests were as follows:

ET 1015=product with guar gum substrate;
ET 1016=product with powdered carob gum substrate;
ET 1017=product with starch substrate;
ET 1018=product with cellulose substrate;
ET 1019=product with tamarind substrate;
ET 1020=product with chitosan substrate;
ET 1021=product with tragacanth substrate.

TABLE 1

Total serous cholesterol values in rats subjected to a Nath diet (Nath and coll., J. Nutrit. 67, 289, 1959) for 30 days and treated with the various products.

|  | Control | Cholestyramine | ET1015 | ET1016 | ET1017 | ET1018 | ET1019 | ET1020 | ET1021 |
|---|---|---|---|---|---|---|---|---|---|
| No. rats | 10 | 10 | 10 | 10 | 10 | 10 | 10 | 10 | 10 |
| mg % | 312 | 148 | 121 | 124 | 117 | 103 | 134 | 90 | 129 |
|  | ±24.7 | ±11.9 | ±10.7 | ±9.4 | ±10.5 | ±6.8 | ±9.7 | ±9.1 | ±10.3 |

TABLE 2

Total serous cholesterol values in rabbits subjected to a cholesterol-enriched diet for 30 days and treated with the various products.

|  | Control | Cholestyramine | ET1015 | ET1016 | ET1017 | ET1018 | ET1019 | ET1020 | ET1021 |
|---|---|---|---|---|---|---|---|---|---|
| No. rabbits | 10 | 10 | 10 | 10 | 10 | 10 | 10 | 10 | 10 |
| mg % | 702 | 269 | 210 | 122 | 193 | 184 | 229 | 172 | 208 |
|  | ±57.6 | ±18.2 | ±16.5 | ±15.9 | ±14.3 | ±13.9 | ±15.1 | ±14.8 | ±15.1 |

From the aforegoing tables it is clear that the quaternary ammonium salts of polysaccharides according to the present invention have greater hypocholesterolemic activity than cholestyramine both in rats and in rabbits subjected to a hypercholesterolemic diet.

I claim:

1. A method of eliciting a hypocholesterolemic effect in a human subject, which comprises orally administering to said subject a hypocholesterolemically effective amount of a quaternary ammonium salt of the formula

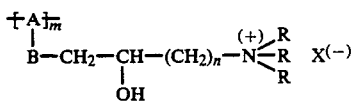

wherein A represents the monomer unit of a natural polysaccharide selected from the group consisting of tragacanth, guar gum, carob gum, starch, tamarind and chitosan;

m is a whole number between 100 and 1,000;

n is a whole number between 0 and 4;

B is selected from the group consisting of O, S, NH and NR;

R is a linear alkyl radical of from 1 to 4 carbon atoms; and

X represents a pharmacologically-acceptable anion; and wherein the degree of substitution on the polysaccharide is between 0.5 and 2.

2. The method of claim 1, wherein X is selected from the group consisting of Cl, Br, I, $HSO_4$ and $CH_3O-SO_3$.

3. The method of claim 1, wherein the natural polysaccharide is tragacanth.

4. The method of claim 1, wherein the natural polysaccharide is guar gum.

5. The method of claim 1, wherein the natural polysaccharide is carob gum.

6. The method of claim 1, wherein the natural polysaccharide is tamarind.

7. The method of claim 1, wherein the natural polysaccharide is chitosan.

8. The method of claim 7, wherein n is 1 and B is selected from the group consisting of O and NH.

9. The method of claim 8, wherein R is methyl.

10. The method of claim 9, wherein the degree of substitution on the polysaccharide is about 1.5.

11. The method of claim 10, wherein said quaternary ammonium salt is prepared from chitosan having a 20% degree of acetylation and which has been prepared by acid hydrolysis.

12. The method of claim 9, wherein X represents $Cl^-$.

13. The method of claim 1, wherein the natural polysaccharide is starch.

* * * * *